United States Patent [19]

Fujimoto et al.

[11] Patent Number: 5,357,805
[45] Date of Patent: Oct. 25, 1994

[54] PRESSURE MEASUREMENT APPARATUS FOR INSPECTING THERAPEUTIC ENERGY WAVES

[75] Inventors: Katsuhiko Fujimoto, Kanagawa; Satoshi Aida, Tokyo; Masamichi Oyanagi; Nobuki Kudo, both of Tochigi, all of Japan

[73] Assignee: Kabushiki Kaisha Toshiba, Kawasaki, Japan

[21] Appl. No.: 868,657

[22] Filed: Apr. 15, 1992

[30] Foreign Application Priority Data

Apr. 15, 1991 [JP] Japan .................................. 3-111045
Mar. 16, 1992 [JP] Japan .................................. 4-055961

[51] Int. Cl.$^5$ ............................................. G01L 7/08
[52] U.S. Cl. ........................................... 73/715; 73/714; 128/660.03; 601/2
[58] Field of Search .................. 73/700, 714, 715, 727, 73/756, 146.2, 146; 338/4, 42; 128/660.03, 24 R

[56] References Cited

U.S. PATENT DOCUMENTS

| 3,878,712 | 4/1975 | Chapin | 73/146 |
|---|---|---|---|
| 4,331,030 | 5/1982 | Webster | 73/146 |
| 4,795,998 | 1/1989 | Dunbar et al. | 338/5 |

FOREIGN PATENT DOCUMENTS

| 0211580 | 2/1987 | European Pat. Off. |
| 0256436 | 2/1988 | European Pat. Off. |
| 0256438 | 2/1988 | European Pat. Off. |
| 842548 | 6/1952 | Fed. Rep. of Germany |
| 929327 | 6/1955 | Fed. Rep. of Germany |

OTHER PUBLICATIONS

Extracorporeal Stone Disintegration Using Piezo Ceramics, US88-31, 1988, pp. 45-50, S. Aida, et al.,: "Fundamental Experiments With Large Piece Piezo-Ceramics".

*Primary Examiner*—Donald Woodiel
*Attorney, Agent, or Firm*—Oblon, Spivak, McClelland, Maier & Neustadt

[57] ABSTRACT

This invention relates to a pressure measurement apparatus for inspecting therapentic energy waves, e.g. shock waves or ultrasonic waves. The pressure measurement apparatus for inspecting focal position and pressure of therapeutic energy waves comprises a pressure sensing sheet which changes visually or electrically according to the pressure, and a marker for setting the focal position, mounted on the pressure sensing sheet. Also, the apparatus for inspecting focal position and pressure of therapeutic energy waves in a water tank, comprises, a pressure sensing sheet which changes visually or electrically according to the pressure, a mount for holding the pressure sensing sheet as a flat shape, a mount holder for holding the mount, a marker for setting the focal position, held above the pressure sensing sheet from the mount holder, and holder means for holding the mount holder into the water tank. It is an object of the present invention to provide a pressure measurement apparatus for inspecting therapeutic energy waves, e.g. shock waves and ultrasonic waves wherein the pressure of the energy waves is measured easily. It is another object of the present invention to provide a pressure measurement apparatus for inspecting therapeutic energy waves, wherein it is easy for the user to judge the focal position.

18 Claims, 14 Drawing Sheets

PRESSURE MEASUREMENT APPARATUS FOR INSPECTING THERAPEUTIC ENERGY WAVES

FIELD OF THE INVENTION

This invention relates to a pressure measurement apparatus for inspecting therapeutic energy waves, especially for inspecting the pressure profile at the focal area and the deviation of the focal point from an actual focal position in a treatment apparatus for using shock wave or ultrasound.

DESCRIPTION OF THE PRIOR ART

Recently, in the field of medical treatment, a shock wave treatment apparatus has been used, e.g. lithotripter for disintegrating calculi in a body. And an ultrasonic treatment apparatus has been used for heating and treating a cancer in a body. In these treatment apparatus, shock waves or ultrasonic waves, which are released from an applicator which consists of concave shaped piezo-ceramics and a water bag containing coupling fluid, are focused to a focal point in a patient's body. The applicator is set so that the focal point of the energy is coincident with a target e.g. stone or cancer. However there are no simple methods to determine whether the apparatus is used at a proper state in which shock waves or ultrasonic waves are irradiated to the target correctly. Therefore, it might happen that medical treatments using these apparatus are not safe and effective.

For example, in lithotripter using shock waves, a sufficient effect of disintegrating calculi (for example, kidney stones) is not obtained when the focal pressure has reduced. And if doctors used the apparatus in which the actual focal position of the shock wave deviates from a focal position marker which is displayed on X-ray images or ultrasonic images, the surrounding tissue would be harmed. Further, if the apparatus was used for long time in unusual state, the life time of the apparatus may be shorted.

Therefore, it is necessary for the user to check periodically the focal position and the pressure profile of the focus.

To measure the pressure profile of focal area in medical treatment apparatus using shock wave, a pressure transducer, e.g. membrane type or a needle type hydrophone is used. Both the membrane type and the needle type hydrophone are discussed in detail in "SHOCK WAVE SENSORS: I. REQUIREMENTS AND DESIGN, Journal of Lithotripsy and Stone Disease Vol. 3, No. 1, 1991". In the membrane type hydrophone which is consisting of electrodes which is arranged of two dimensions on a membrane type piezo-electric film in particular, a pressure profile was decided by exposing only once. But it was difficult to detect the pressure sensing point of the membrane type hydrophone using ultrasound or X-ray imaging apparatus because a pressure sensing point of that hydrophone can't be invisible to those imaging apparatus. In short, it is difficult for the user to know the deviation between the actual focal position of the applicator and the imaging focal position.

On the other hand, in the needle type hydrophone (e.g. IMOTEC Corp.—made piezo-electric type mini pressure pickup: Type 80—0.5—40), it is easy to detect the sensor position using ultrasound and X-ray imaging apparatus. But the needle type—hydrophone is broken easily, so that the number of shock wave measurement is restricted. As a result, the needle type—hydrophone couldn't detect the pressure profile of the focal area because it needs many measurement points. Therefore, it is difficult to detect the deviation between the actual focal position of the applicator and the imaging focal position using the needle typehydrophone.

As mentioned above, in the prior art, the pressure measurement apparatus for inspecting shock wave has both merits and demerits. If the actual focal position of the applicatior coincides with the focal position on the image display for target localization, the pressure of focal position is measured exactly using a hydrophone. But if the actual focal position of the applicator deviates from the focal position on the image display, the pressure measurement of the direction and the distance of the deviation between the actual focal position of the applicator and the focal position on the image display is very complicated. Thus it is difficult for the user to judge the focal position.

SUMMARY OF THE INVENTION

It is an object of the present invention to provide a pressure measurement apparatus for inspecting therapeutic energy waves, which makes it easy for the user to judge the focal position.

The pressure measurement apparatus for inspecting therapeutic energy waves comprises a pressure sensing sheet which changes visually or electrically according to the pressure of the energy waves and a marker for being set to the focal position on display imaging, which is mounted on the pressure sensing sheet.

The pressure measurment apparatus for inspecting therapeutic energy waves further comprises a mount for holding the pressure sensing sheet flat, a mount holder for holding the mount, a marker for being set to the focal position held above the pressure sensing sheet, and a holder means for holding the mount holder in a water tank.

DETAILED DESCRIPTION OF THE INVENTION

An embodiment of the present invention will be described hereinafter with reference to the accompanying drawings.

Figure 1:
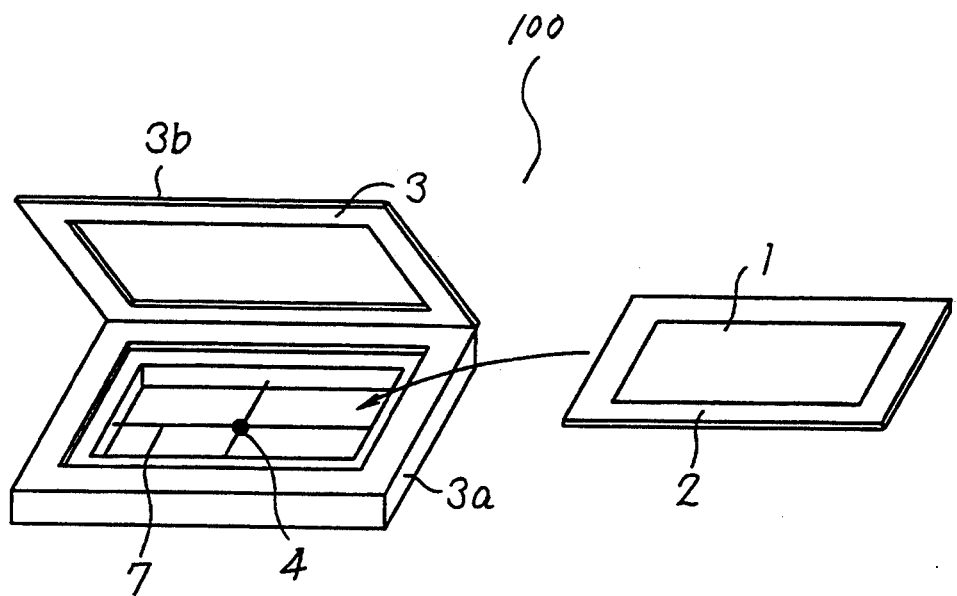
FIG. 1 shows a pressure measurement apparatus according to an embodiment of the present invention.

The pressure measurment apparatus in FIG. 1 comprises a pressure sensing sheet 1, a mount for pressure sensing sheet 2, a mount holder 3 and a marker 4. The pressure sensing sheet 1 consists of a pressure sensing paper 5 whose color is changed partially by additional pressure thereon, and a transparent sticky tape for water-proof. The pressure sensing paper 5 is e.g. FUJI FILM Corp.—made prescales and 0.045 by 0.04 m.

The mount for pressure sensing sheet 2 has a similar structure to a mount for slides which are marketed. The mount for pressure sensing sheet 2 retains the pressure sensing sheet 1 in a flat shape. The pressure sensing sheet 1 is exchanged for recycling. Further the mount for pressure sensing sheet 2 may be a disposable type which retains the pressure sensing sheet 1.

The mount holder 3 holds the mount for pressure sensing sheet 2. The mount holder 3 consist of box portion 3a which is a flat shape and a cap portion 3b. The box portion 3a has a step for retaining the mount for pressure sensing sheet 2. The mount for pressure sensing sheet 2 is clipped by the box portion 3a and the cap portion 3b. The marker 4 is used to set a position of ultrasonic and/or X-rays. The marker 4 is a small radio-opaque, which is e.g. glass, titanium (Ti), iron (Fe), tin (Sn), tungsten (W) and tantalum (Ta). The marker 4 is retained at the center of the open side of the mount holder 3 by wire 7, which has nearly the acoustic impedance of water and is radio—lucent, e.g. rubber, glass, silicon (Si) and polyester. In this case, the marker 4 is held above the pressure sensing sheet 1. If the marker 4 contacts the pressure sensing sheet 1, when the shock wave exposes the pressure sensing sheet 1, a reflection could cause contact between the pressure sensing sheet 1 and the marker 4. As a result, it is impossible to exactly by measure the focal pressure.

When the pressure of a shock wave is measured by using the pressure measurement apparatus, the pressure measurement apparatus is held in a water tank by a holder. The pressure measurement apparatus is exposed to the shock wave by the shock wave source 23, which is an applicator of a water bag type.

Figure 3:
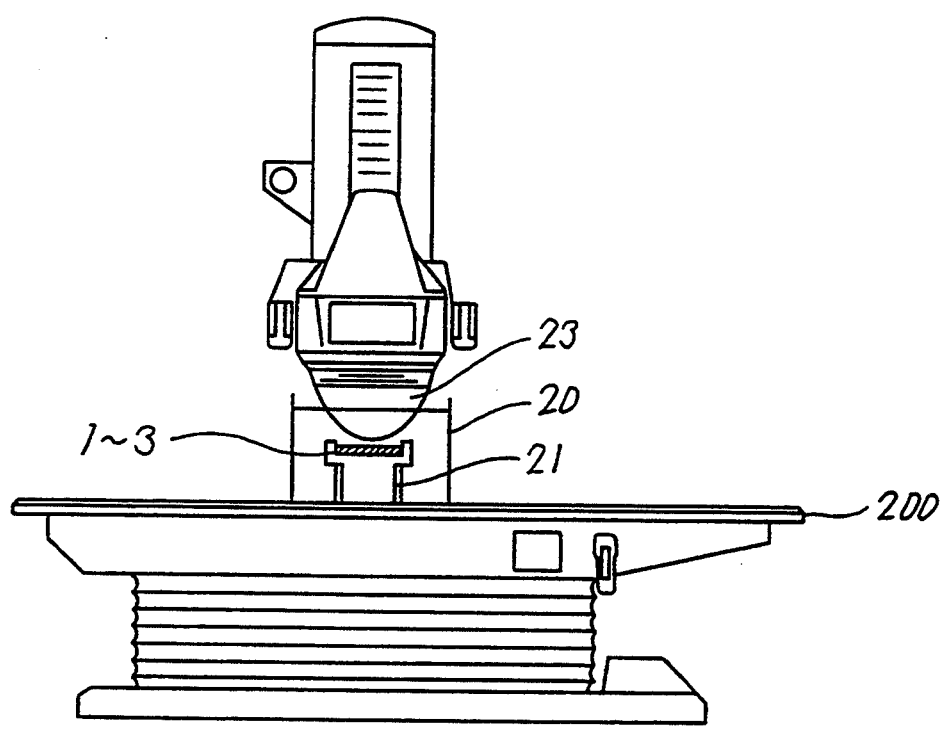
FIG. 3 is a side figure showing the pressure measurement apparatus, which is used in a shock wave treatment apparatus according to the embodiment of the invention.

FIG. 3 shows the pressure mesurement apparatus of the present invention which is established in the shock wave treatment apparatus. As shown in the FIG. 3, the pressure sensing sheet 1, the mount 2 and the mount holder 3 are mounted in the water tank 20 by holder 21. When the pressure measurement apparatus measures the focal position of the shock wave source 23, the pressure measurment apparatus must be in a set position.

FIG. 4 relates the focal position marker 50 on the image display 60, which is used to set the focal position of the lithotripter and color emitting state. FIGS. 4A and 4B show that the actual focal position of shock wave (i.e. spot 80) coincides with the focal position marker 50 on image display 60. FIG. 4B shows the relative position of the focal position of the shock wave in the pressure sensing sheet 1 and marker 4. Further, the position is set by using X-rays, because the marker 4 is radio-opaque.

Figure 4A:
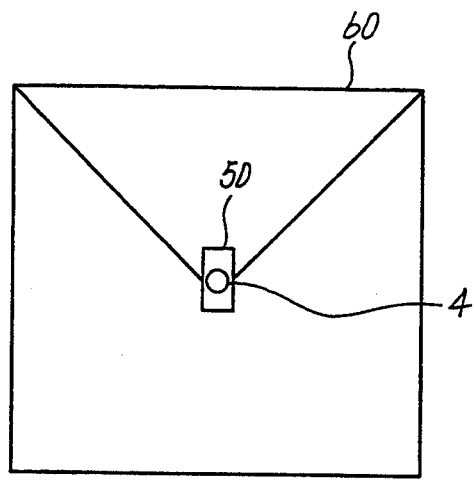
FIGS. 4A, 4B, 4C and 4D shows the relationship between the focal position marker on an image display and a color emitting state.
Figure 4B:
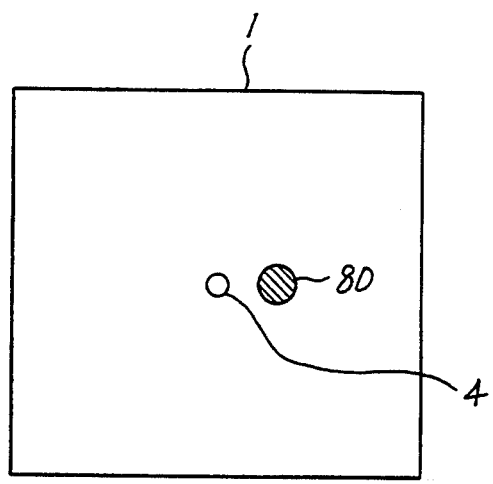
Figure 4C:
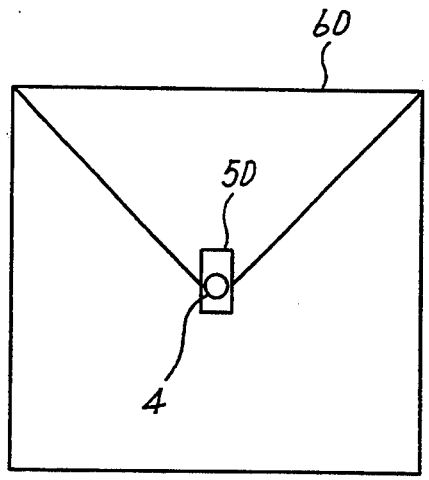
Figure 4D:
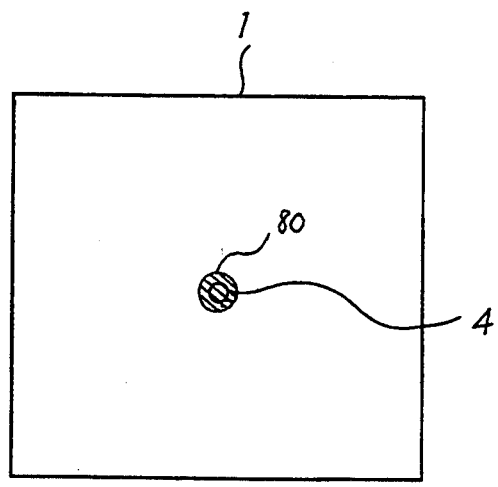

The position is set as the marker 4 coincides with the focal position marker 50. But actually, the spot 80 deviates from the marker 4. After the position is set according to distance and direction between the marker 4 and the spot 80 on the pressure sensing sheet 1, the shock wave source 23 is operated. In this way, the user sets the focal position by referring to the deviation of the spot 80 on the pressure sensing sheet 1. Finally, as shown in FIGS. 4C and 4D, the spot 80 coincides with the focal position marker 50 and the marker 4.

As mentioned above FIG. 4 shows the set position of the marker 4 which is coincident with the focal position marker 50 on the image display 60. Also this invention operates to adjust the focus pressure to the most suitable pressure. Concretely speaking, when the maximum pressure of the focal position, which is guaranteed by the shock wave treatment apparatus, comes down 0%,, 10%, 20% and 30% respectively, each color emitting state is recorded as a standard color emitting state.

Figure 5A:
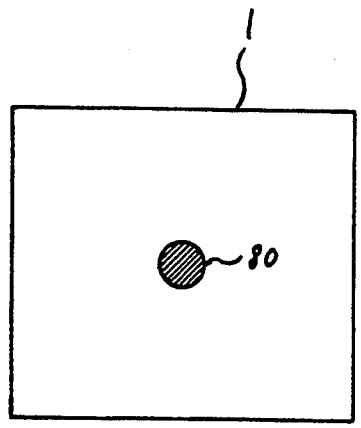
FIGS. 5A, 5B, 5C and 5D illustrate how the color changes when the shock wave has less energy.
Figure 5B:
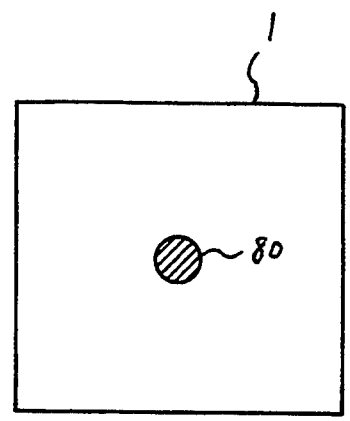
Figure 5C:
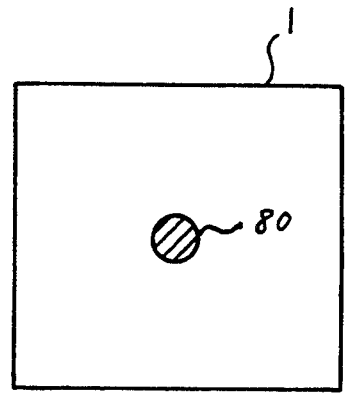
Figure 5D:
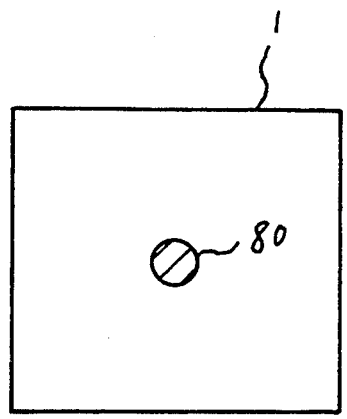
Figure 6A:
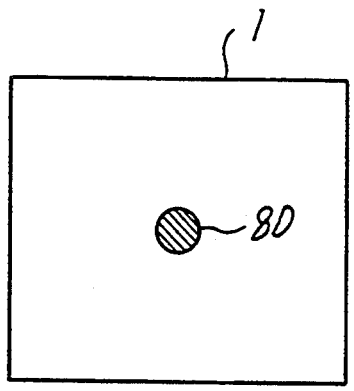
FIGS. 6A–6D illustrate how the size of the color changes when the shock wave has less energy.
Figure 6B:
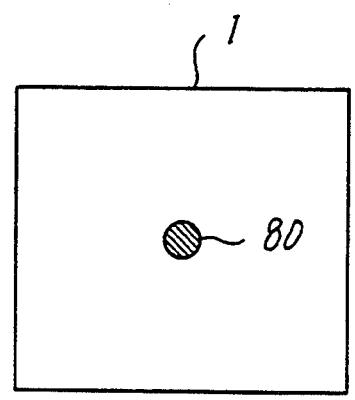
Figure 6C:
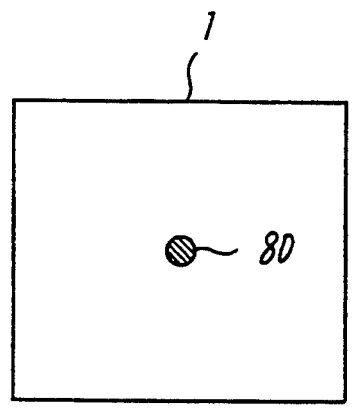
Figure 6D:
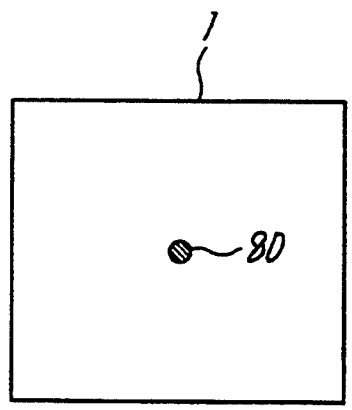

FIGS. 5A and 6A show the color emitting state of the pressure sensing sheet 1, when the maximum pressure of the focal position comes down. FIG. 5B shows the color emitting state when the pressure value comes down 10% from the maximum pressure. FIG. 5C shows the color emitting state when the pressure value comes down 20% from the maximum. FIG. 5D shows the color emitting state when the pressure value comes down 30% from the maximum. FIG. 6 is different from the FIG. 5, in that FIG. 5 shows, when the maximum pressure comes down, the color is more light, but in FIG. 6, when the maximum pressure comes down, the color area is smaller. Thus, the user compares the actual color emitting area with a standard color emitting which was previously recorded as the maximum pressure, when the shock wave treatment apparatus is inspected by the user. The user can judge how much the pressure has come down. As a result, the user can decide whether the actual maximum pressure is enough, and whether a serviceman must examine the shock wave treatment apparatus.

Figure 7:
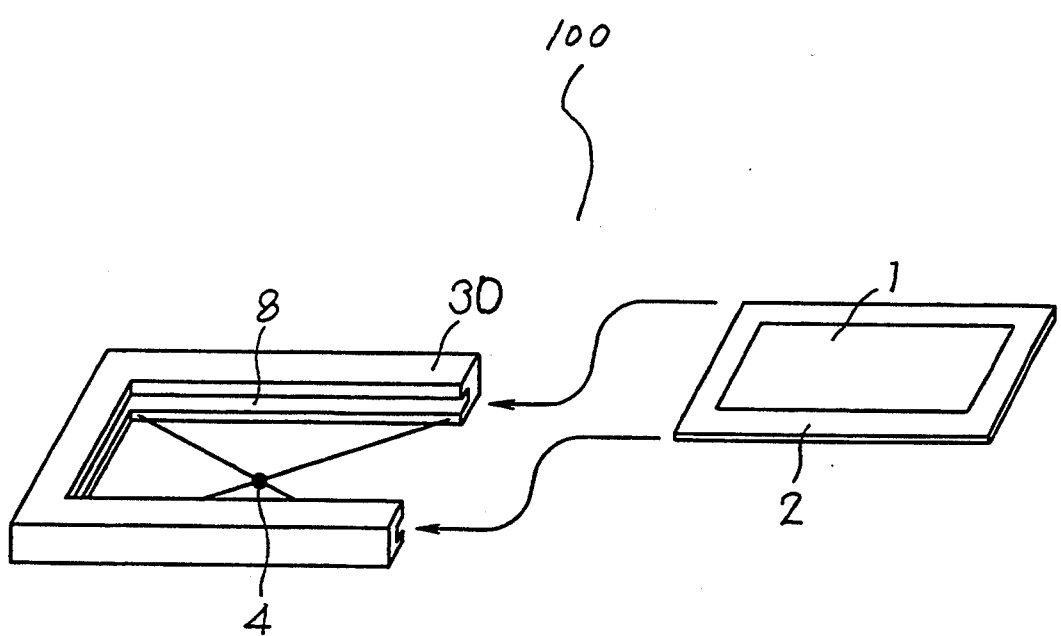
FIG. 7 shows a pressure measurement apparatus according to another embodiment of the invention.

FIG. 7 shows another embodiment of the pressure measure apparatus according to the present invention, which is different from the mount holder 3 of the FIG. 1. The mount holder 3 consists of a frame, which has an opening side and has gutter 8 to insert the mount of the pressure sensing sheet 2 from the opening side, as shown pointing arrow in FIG. 7.

Figure 2:
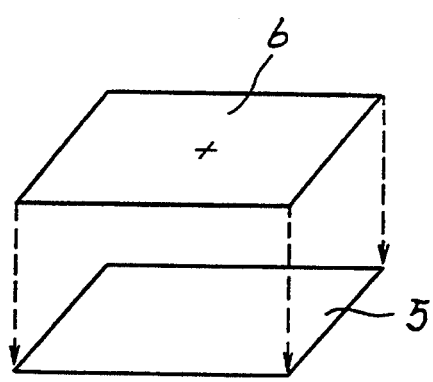
FIG. 2 shows a pressure sensing sheet shown in FIG. 1.
Figure 8:
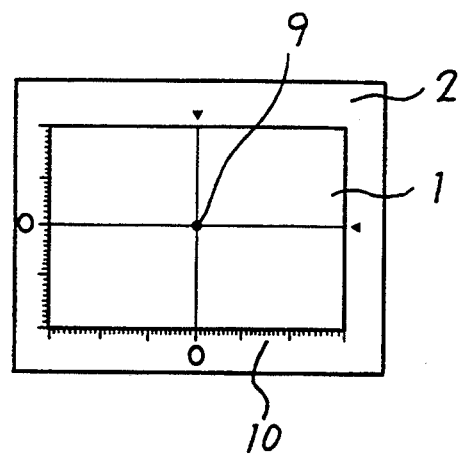
FIG. 8 shows a mount for a pressure sensing sheet shown in FIG. 1.
Figure 9:
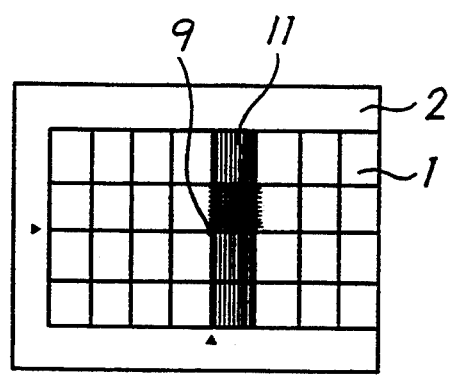
FIG. 9 shows another mount for a pressure sensing sheet shown in FIG. 7.

FIGS. 8 and 9 show other embodiments of the pressure sensing sheet 1 and the mount for pressure sensing sheet 2. As shown in FIG. 8, an indication mark for focal position 9 has a different color (e.g. blue, if the color of the pressure sensing paper 5 is red) from the color of the pressure sensing paper 5. The indication marker 9 is marked on the surface of transparent tape 6, which contacts the pressure sensing sheet 1 as shown FIG. 2, and the marker 4. The indication mark for focal position 9 is e.g. a dot, a cross or two stright lines, and the cross point indicates focal position.

In this case, the mount for pressure sensing sheet 2 has scale 10, which has a zero point corresponding to the focal position for focal position 9. As a result, deviation of actual focal position and geometric focal position may be measured by user quantitatively.

As shown in FIG. 9, cross hair 11 is printed on the pressure sensing sheet 1. The zero point of the cross hair 11 is the focal position of the indication mark 9. In these ways, the effect of this case is the same as that of FIG. 8.

FIGS. 10-14 show the embodiment in which the pressure measurement apparatus of the present invention is actually applied to the shock wave treatment apparatus.

Figure 10:
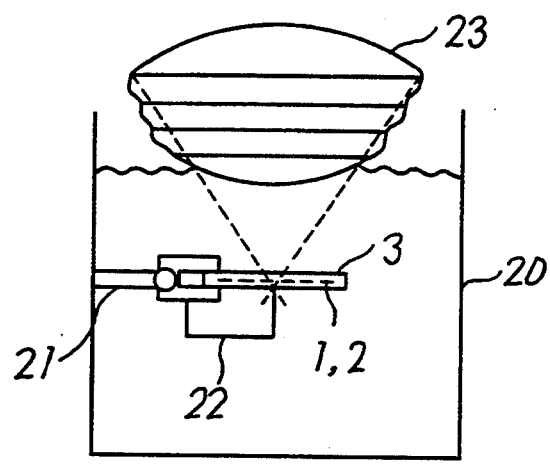
FIG. 10 shows an arrangement for the pressure sensing sheet shown in FIG. 1.

As shown in FIG. 10, the pressure measurement apparatus is established horizontally and the pressure sensing sheet is established perpendicular to the focus direction of the shock wave by holder 21 in the water tank 20. The point of the shock wave source 23 is dipped in the water bag and the pressure measurement apparatus measures the focal position pressure for the shock wave irradiated from the shock wave source 23. In this case, the water tank 20 or the holder 21, which is on the marker, may be used.

Figure 11:
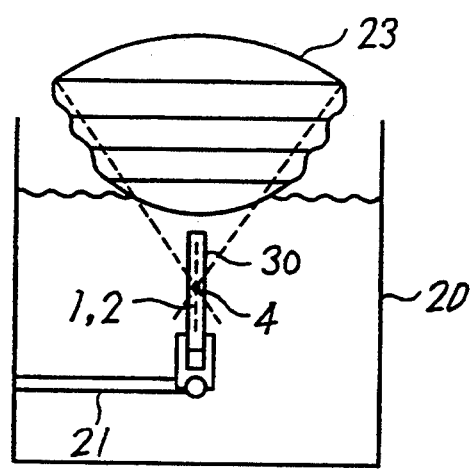
FIG. 11 shows another arrangement for the pressure sensing sheet shown in FIG. 9.

FIG. 11 shows another embodiment different from FIG. 10. The pressure measurement apparatus is established vertically, in other word parallel to the focus direction of the shock wave.

In this case, the mount for pressure sensing sheet 2, whose one side is removed as shown in FIG. 9, is adopted and the mount holder 3, whose one side is removed. As shown in FIG. 7, is adopted, the pressure sensing sheet 1 is set parallel to the focus direction of shock wave and the pressure measurement apparatus can measure the pressure distribution in the focus direction of the shock wave.

Figure 12:
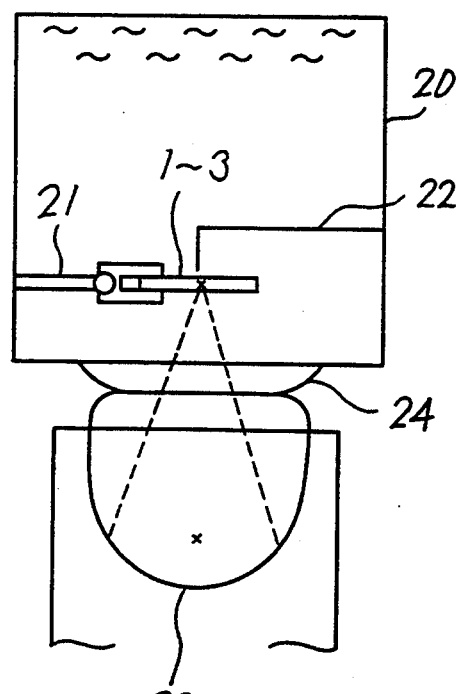
FIG. 12 shows an arrangement for the pressure measurement apparatus according to the base contact shock wave source.

FIG. 12 shows another embodiment wherein shock wave source 23 contacts a membrane 24, which is established on the base of the water tank 20.

Figure 13:
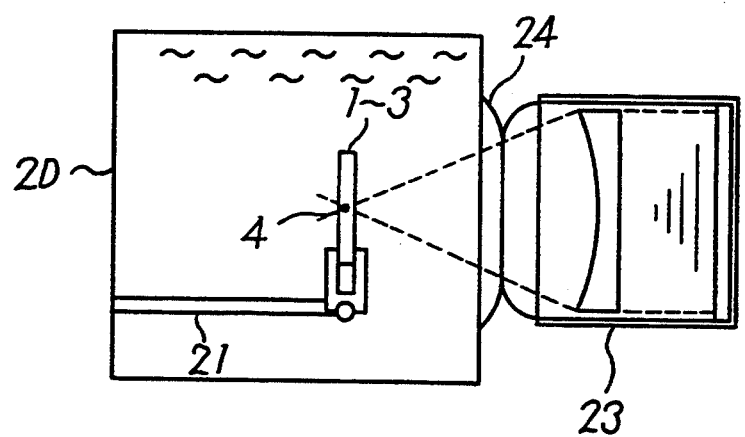
FIG. 13 shows another arrangement for the pressure measurement apparatus according to the base contact shock wave source.

FIG. 13 shows another embodiment wherein shock wave source 23 contacts a membrane 24, which is established on the side of the water tank 20.

Figure 14:
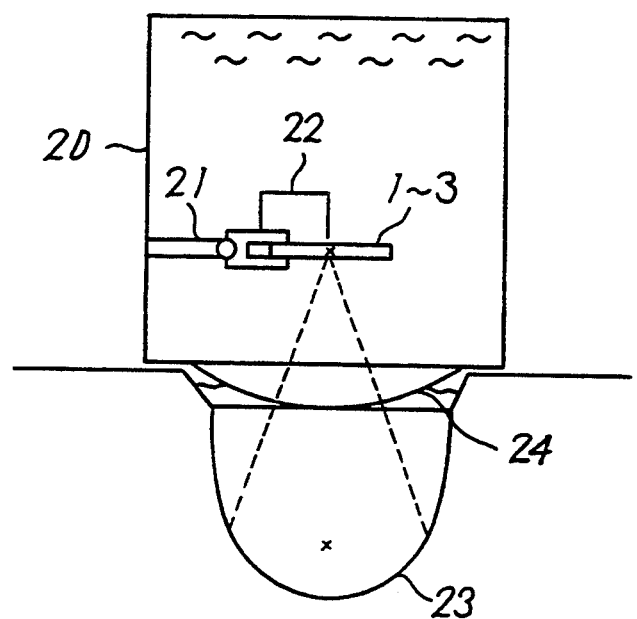
FIG. 14 shows an arrangement for the pressure measurement apparatus using an open type lithotripter which has a base contact shock wave source.

FIG. 14 shows another embodiment applied to an open type lithotripter. This case which is similar to FIG. 12, shows shock wave source 23 contacting a membrane 24, which is established on the base of the water tank 20.

The embodiments in FIG. 11 and FIG. 13 show the small ball as the marker 4. But in the embodiments shown in FIGS. 10, 12 and 14, in which the pressure measurement apparatus is established horizontally, it is possible to hold needle type marker 22 to the water tank 20 or holder 21 without contacting the pressure sensing sheet 1.

Figure 15:
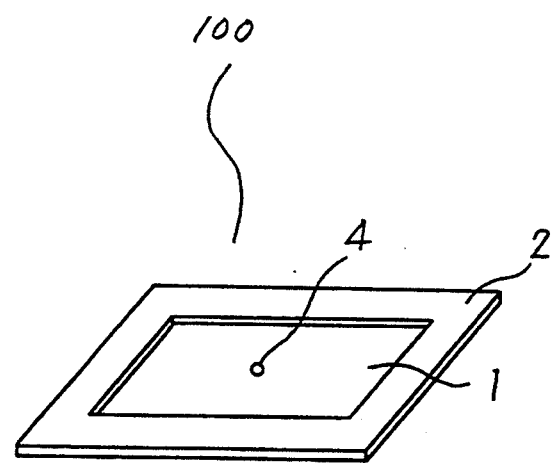
FIG. 15 shows an arrangement for a marker according to an embodiment of the present invention.

In above embodiment, the marker 4 (22) was established at the back of the pressure sensing sheet 1, which is opposite to the side of the shock wave source. But as for the lithotripter which is an ultrasonic portrait type, the ultrasonic is reflected in front of the pressure sensing sheet 1. Thus, it often happens that the marker 4 at the back of the pressure sensing sheet 1 is not visible. In this case, to confirm position setting accuracy, the marker 4 is established in front of the pressure sensing sheet 1. In this method, the marker 4 is held on the surface of the pressure sensing sheet 1 by adhesive agent, as shown in FIG. 15.

However, if the marker 4 is established in front of the pressure sensing sheet 1, pressure distribution on the surface of the pressure sensing sheet 1 is confused. Therefore, the accuracy of pressure measurment value comes down. Thus, as shown in FIG. 8 and FIG. 9, a pressure sensing sheet 1 which has a mark for focal position 9 indicated on the pressure sensing paper 5, is adopted. The marker 4 is fixed at the center of the front of the pressure sensing sheet 1. The user then sets the focal position for the lithotriper according to the marker 4. When strong ultrasonic for treatment is used, the marker 4 is removed from the pressure sensing sheet 1. Such being the case, confusion of pressure distribution on the front surface of the pressure sensing sheet 1 disappears and it is possible to set the focal position and measure the pressure value exactly.

Figure 16:
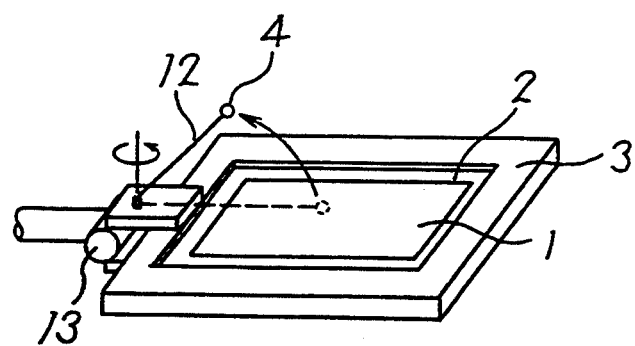
FIG. 16 shows another arrangement for an marker according to an embodiment of the present invention.

FIG. 16 shows the embodiment of the pressure measurment apparatus, which is applied to this method. The pressure measurment apparatus prepares the marker 4, which is mounted on top of thin arm 12 and the arm 12 is mounted on driving mechanism 13, which can rotate. If the arm 12 is rotated by the driving mechanism 13, marker 4 is set in front of the pressure sensing sheet 1 and is detached from front of the pressure sensing sheet 1.

Figure 17:
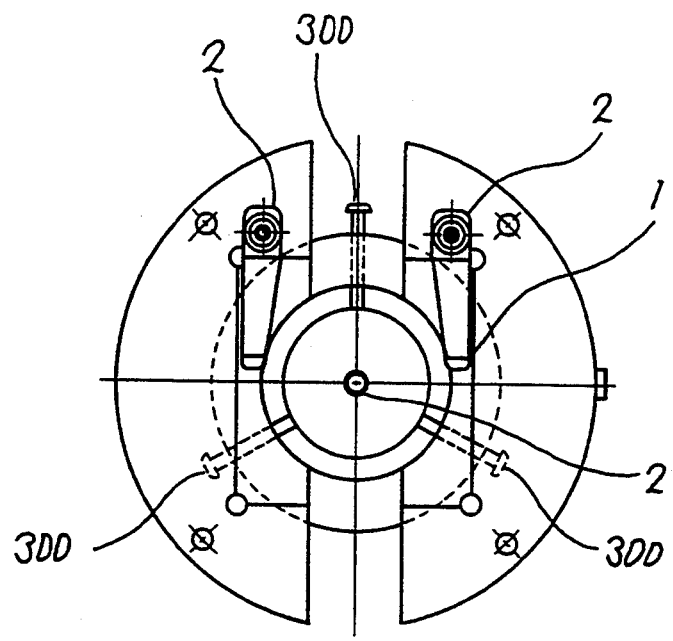
FIG. 17A shows an arrangement for a marker according to another embodiment of the invention.
FIG. 17B shows an arrangement for a marker according to another embodiment of the invention.
Figure 17:
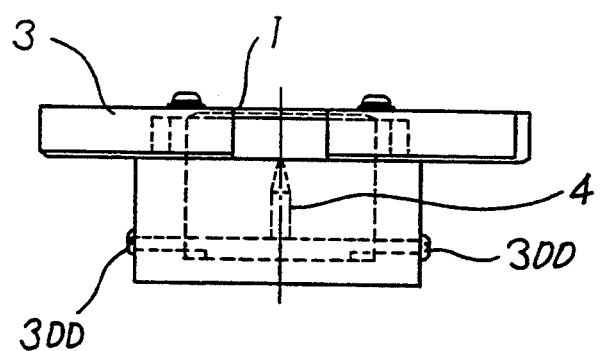

More, FIG. 17 shows another embodiment in that the marker 4, which is a needle type, contacts the back of the pressure sensing sheet 1. FIG. 17A shows a diagram on the top view of the pressure measurement apparatus in this embodiment. FIG. 17B shows a diagram on the side view of the pressure measurement apparatus in this embodiment. In this case, the pressure measurement apparatus is established in a water bag and the focal position of the shock wave source is set so that the focal position coincides with the focal position marker (NOT shown) in the ultrasonic portrait. In this state, if the shock wave is exposed, a color emitting point corresponding to the pressure of the shock wave appears on the pressure sensing sheet 1.

Then an object (an innerprove)is pushed against the pressure sensing sheet 1, which contacts the marker 4. As a result, a point, between the innerprove and the marker 4, appears as a strong color emitting point. Thus, if the interval between two color emitting points on the pressure sensing sheet 1 is measured, the deviation between the focal point of the shock wave source and the marker 4 is detected exactly. Futher the deviation is detected by holding up the pressure sensing sheet 1 to light. It is also detected by lighting from the opposite surface of the pressure sensing sheet 1.

Figure 18:
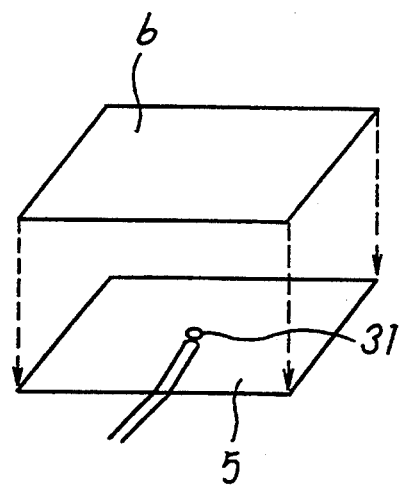
FIG. 18 shows another pressure sensing sheet for applying a pressure transducer.
Figure 19:
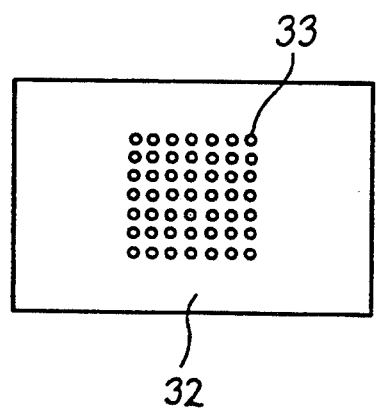
FIG. 19 shows yet another pressure sensing sheet for applying a membrane type piezo-electric film.

Next, FIGS. 18 and 19 show the other embodiment of the pressure sensing sheet. As shown in FIG. 18, the pressure transducer 31, which is a small membrane type, is held by the transparent sticky tape for water-proof 6 on the pressure sensing paper 5. Using this system, even if the focal position corresponding to the marker 4 and focal position corresponding to the shock wave are different, the deviation of detection and quantity is detected easily. Accordingly, by the user can revise the deviation. After that, by emitting the shock wave, the pressure measurement apparatus can measure the focal position pressure exactly.

FIG. 19 shows a pressure sensing sheet which is a hydrophone consisting of electrodes 33 arranged by the same interval on a membrane type piezo-electric film 32. In the pressure sensing sheet, when the shock wave is irradiated to the film 32, an electric signal, which has a different level corresponding to the pressure distribution of the shock wave, is gained from the electrode as the output of the hydrophone. Therefore, according to the output of the hydrophone, the sound field, or peak pressure in the focal position, still more deviation between the focal position corresponding to the relative position of the applicator and the actual focal position, are measured. As for the value of these measurement which result, the user can understand whether the output will break the calculus can judge if the treatment apparatus is operating properly and can detect any unusual output easily.

The pressure sensing sheet has pressure a sensible extent of e.g. 50–100 Mpa. But it often happens that the shock wave irradiated by lithotoripter is not within the pressure sensible extent.

For example, when the maximum output of the shock wave is 1200 Mpa, even if the maximum output of the shock wave goes down 20%, the pressure sensing sheet can't detect the change. Conversely, when the maximum output of the shock wave is 40 Mpa, the pressure sensing sheet will not detect this level, so that it is impossible to measure. In this case, pressure sensing sheets, as shown in FIGS. 20 or 21, are suitable ones.

Figure 20:
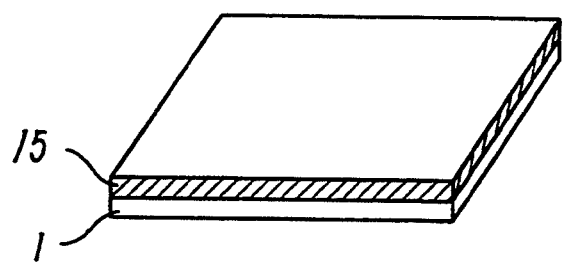
FIG. 20 shows a pressure sensing sheet on which a damping film is used.

FIG. 20 shows pressure sensing sheet for high-pressure. In FIG. 20, on the front surface of the pressure sensing sheet 1, a damping film 15, e.g. a rubber sheet, is adhered. The space between the damping film 15 and the pressure sensing sheet 1 is a vacuum. If the pressure sensing sheet is used in the same manner the earlier described embodiment, the transparency output of shock wave decreases by 20%, so the pressure sensing sheet can detect the maximum output of 120 Mpa of lithotripter. Further, by choosing the acoustic characteristics, a suitable damping quantity is set up for the damping film 15.

Figure 21:
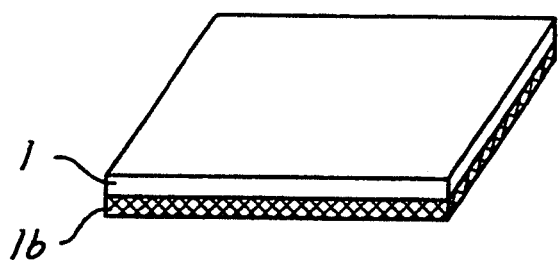
FIG. 21 shows a pressure sensing sheet, on which a reflecting film is used.

FIG. 21 shows a pressure sensing sheet for low-pressure. In FIG. 21, on the back surface of the pressure sensing sheet 1, a reflection film 16 which has an acoustic impedance more than that of the sensing sheet 1, e.g. stainless, is adhered. The space between the reflection film 16 and the pressure sensing sheet 1 is a vacuum. If the pressure sensing sheet is used in the described embodiments, the output of the shock wave may be increase by 50%, so the pressure sensing sheet may be used for the maximum output 40 Mpma of lithotoripter.

Further the pressure sensing paper 5 may be exchanged for heat sensing paper. Thus, a heat sensing sheet, when the heat sensing paper is adopted, can apply for inspection of ultrasonic treatment apparatus for hyperthermia.

What is claimed is:

1. A pressure measurement apparatus for inspecting the focal position and the pressure of therapeutic energy waves, comprising:

a pressure sensing sheet whose color, or electrical conductivity changes when pressure is applied to it; and a marker for setting the focal position, said marker being mounted near said pressure sensing sheet.

2. An apparatus according to claim 1, further comprising:

a first mount for holding said pressure sensing sheet in a flat shape; and a second mount holder for holding said first mount.

3. An apparatus according to claim 2, wherein said first mount includes scales for focal position setting, which are mounted on a surface of said pressure sensing sheet.

4. An apparatus according to claim 2, further comprising:

marker holding means for holding said marker above said pressure sensing sheet said marker holding means being connected to one of said first mount and said second mount.

5. An apparatus according to claim 4, wherein said marker hold means holds said marker at the center of an open space of said first mount holder above said pressure sensing sheet.

6. An apparatus according to claim 4, wherein said marker holding means comprises material whose acoustic impedance is similar to water, or which is transparent to X-rays.

7. An apparatus according to claim 2, wherein said marker is a needle type marker and is mounted on said first mount holder so that the point of said marker contacts the back surface of said pressure sensing sheet and said needle type marker is oriented with its long axis perpendicular to the pressure sensing sheet.

8. An apparatus according to claim 1, wherein said pressure sensing sheet comprises pressure sensing paper whose color is a function of pressure that is applied to it; and transparent sticky tape for water-proofing that is mounted on said pressure sensing paper.

9. An apparatus according to claim 1, further comprising:

a means for generating the energy waves and directing the energy waves towards the pressure sensing sheet; and wherein said marker is mounted adjacent a back side of said pressure sensing sheet with respect to a direction of propagation of the energy waves.

10. An apparatus according to claim 1, wherein said marker comprises material which is radio-opaque.

11. An apparatus according to claim 1, further comprising:

marker driving means for holding said marker adjacent said pressure sensing sheet, and for removing said marker from adjacent said pressure sensing sheet.

12. An apparatus according to claim 11, wherein said pressure sensing sheet includes an indication mark that is useful for setting the focal position when said marker is removed from adjacent said pressure sensing sheet.

13. An apparatus according to claim 2, wherein said first mount holder comprises a frame including an open side and a gutter to insert said mount from said open side.

14. An apparatus according to claim 1, further comprising:

a pressure damping film, which is adhered to a surface of said pressure sensing sheet, whereby said pressure damping film decreases pressure on said pressure sensing sheet due to the energy waves.

15. An apparatus according to claim 1, further comprising:
a pressure reflection film, which is adhered to a surface of said pressure sensing sheet, whereby said pressure reflection film increases pressure due to the energy waves on said pressure sensing sheet.

16. A pressure measurement apparatus for inspecting the focal position and the pressure of therapeutic energy waves in a water tank, comprising:
a pressure sensing sheet whose color changes according to pressure applied to it;
a mount for holding said pressure sensing sheet in a flat shape;
a mount holder for holding said first mount;
a marker for setting said focal position that is held above said pressure sensing sheet by said mount holder; and
holder means for holding said mount holder in said water tank.

17. A pressure measurement apparatus for inspecting the focal position and pressure at the focal position that is due to converging pressure waves, comprising:
a pressure sensing sheet whose color is a function of pressure that is applied to it;
means for generating the converging pressure waves; and
means for holding the pressure sensing sheet flat and in the path of the converging pressure waves.

18. A device according to claim 17, further comprising a marker positioned near the pressure sensing sheet for aligning the pressure sensing sheet with a focal position of the converging energy waves.

* * * * *